(12) United States Patent
Haynie

(10) Patent No.: US 7,973,129 B2
(45) Date of Patent: *Jul. 5, 2011

(54) POLYPEPTIDE FILMS AND METHODS

(75) Inventor: Donald Templeton Haynie, Tampa, FL (US)

(73) Assignee: Artificial Cell Technologies, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/754,085

(22) Filed: Apr. 5, 2010

(65) Prior Publication Data

US 2010/0189769 A1  Jul. 29, 2010

Related U.S. Application Data

(63) Continuation of application No. 12/017,630, filed on Jan. 22, 2008, now Pat. No. 7,759,305.

(60) Provisional application No. 60/886,021, filed on Jan. 22, 2007.

(51) Int. Cl.
*C07K 2/00* (2006.01)
(52) U.S. Cl. ..................................... 530/300
(58) Field of Classification Search .................... None
See application file for complete search history.

(56) References Cited

U.S. PATENT DOCUMENTS

| | | | |
|---|---|---|---|
| 6,020,175 A | 2/2000 | Onda et al. | |
| 6,479,146 B1 | 11/2002 | Caruso et al. | |
| 7,550,557 B2 * | 6/2009 | Haynie | 530/300 |
| 7,662,911 B2 * | 2/2010 | Haynie et al. | 530/300 |
| 7,759,305 B2 * | 7/2010 | Haynie | 514/2 |
| 2004/0013721 A1 | 1/2004 | Antipov et al. | |
| 2005/0069950 A1* | 3/2005 | Haynie | 435/7.1 |
| 2005/0180945 A1 | 8/2005 | Chaikof et al. | |
| 2007/0207212 A1* | 9/2007 | Haynie et al. | 424/490 |

FOREIGN PATENT DOCUMENTS

WO   WO 2008013558 A2 *  1/2008

OTHER PUBLICATIONS

Chluba et al. "Peptide Hormone Covalently Bound to Polyelectrolytes and Embedded into Multilayer Architectures Conserving Full Biological Activity," Biomacromolecules, 2001, 2, 800-805.*
Thierry et al. "Delivery Platform for Hydrophobic Drugs: Prodrug Approach Combined with Self-Assembled Multilayers," J. Am. Chem. Soc., 2005, 127, 1626-1627.*
Li et al. "Complete Regression of Well-established Tumors Using a Novel Water-soluble Poly(L-Glutamic Acid)-Paclitaxel Conjugate," Cancer Research, 1998, 58, 2404-2409.*
Vodouhe et al. "Control of drug accessibility on functional polyelectrolyte multilayer films," Biomaterials, 2006, 27, 4149-4156.*
Thierry et al. "Bioactive Coatings of Endovascular Stents Based on Polyelectrolyte Multilayers," Biomacromolecules, 2003, 4, 1564-71.*
Etienne et al. "Antifungal coating by biofunctionalized polyelectrolyte multilayered films," Biomaterials, 2005, 26, 6704-6712.*
Etienne et al. "Multilayer Polyelectrolyte Films Functionalized by Insertion of Defensin: a New Approach to Protection of Implants from Bacterial Colonization," Antimicrobial Agents and Chemotherapy, 2004, 48, 3662-3669.*
International Search Report and Written Opinion; International Application No. PCT/US2008/000805; International Filing Date Jan. 22, 2008; Date of Mailing Jul. 11, 2008; 13 pages.
Haynie, et al.; "Protein-Inspired Multilayer Nanofilms: Science, Technology and Medicine"; Nanomedicine: Nanotechnology, Biology, and Medicine; 2; pp. 150-157; (2006).
Zheng, et al.; "Design of Peptides for Thin Films, Coatings and Microcapsules for Applictions in Biotechnology"; J. Biomater: Sci. Polymer Edn.; 16; pp. 285-299; (2005).
Haynie, et al.; "Polypeptide Multilayer Films: Role of Molecular Structure and Charge"; Langmuir; 20; pp. 4540-4547; (2004).
Schultz et al.; "Polyelectrolyte Multilayers Functionalized by a Synthetic Analogue of an Anti-Inflammatory Peptide, a-MSH, for Coating a Trachael Prosthesis"; Biomaterials; 26; pp. 2621-2630; (2005).
Shneider et al., "Multifunctional Polyelectrolyte Multilayer Films: Combining Mechanical Resistance, Biodegradability, and Bioactivity"; Biomacromolecules; 8; pp. 139-145; (2007).

* cited by examiner

Primary Examiner — Christina Bradley
(74) Attorney, Agent, or Firm — Cantor Colburn LLP

(57) ABSTRACT

Disclosed herein are polypeptide multilayer films wherein a therapeutic agent is covalently linked to a first layer polypeptide. An advantage of such attachment is that the linked therapeutic agent can be controllably released from the multilayer film into the environment of the film upon the addition of a suitable stimulus. An advantage of the disclosed films and methods is enablement of environmentally-stimulated release under specific conditions.

18 Claims, 5 Drawing Sheets

Layer-by-Layer Self-Assembly (LBL) of Multilayer Films

1　　　　2　　　　3　　　　4

Film Formed on a Planar Substrate (Coating)

Film Formed on a Spherical Template (Capsule)

POLYPEPTIDE FILMS AND METHODS

CROSS-REFERENCE TO RELATED APPLICATIONS

This application is a continuation of U.S. application Ser. No. 12/017,630, filed Jan. 22, 2008, which claims the benefits of U.S. Provisional Patent Application Ser. No. 60/886,021 filed Jan. 22, 2007, which is fully incorporated herein by reference.

BACKGROUND

Polyelectrolyte multilayer films are thin films (e.g., a few nanometers to millimeters thick) composed of alternating layers of oppositely charged polyelectrolytes. Such films can be formed by layer-by-layer assembly on a suitable substrate. In electrostatic layer-by-layer self-assembly ("ELBL"), the physical basis of association of polyelectrolytes is electrostatics. Film buildup is possible because the sign of the surface charge density of the film reverses on deposition of successive layers. The general principle of ELBL deposition of oppositely charged polyions is illustrated in FIG. 1. The generality and relative simplicity of the ELBL film process permits the deposition of many different types of polyelectrolytes onto many different types of surface. Polypeptide multilayer films are a subset of polyelectrolyte multilayer films, comprising at least one layer comprising a charged polypeptide. A key advantage of polypeptide multilayer films is environmental benignity. ELBL films can also be used for encapsulation. Applications of polypeptide films and microcapsules include, for example, nano-reactors, biosensors, artificial cells, and drug delivery vehicles.

The design principles for incorporation of polypeptides into multilayer films were first elucidated in U.S. Patent Publication No. 20050069950. In brief, the suitability of a polypeptide for ELBL is related to the net charge on the polypeptide and the length of the polypeptide. A polypeptide suitable for ELBL preferably comprises one or more amino acid sequence motifs, that is, contiguous amino acid sequences having a length of about 5 to about 15 amino acid residues and having a suitable linear charge density for electrostatic deposition. A polypeptide for ELBL can be designed in different ways, for example, by joining a plurality of amino acid sequence motifs to each other, either directly, or by a linker. Polypeptides having the appropriate length and charge properties can readily be deposited to form one or more layers of a polypeptide multilayer film.

Although the basic design principles for polypeptide multilayer films have been elucidated, there nonetheless remains a need for design of polypeptide multilayer films having a desired functionality, particularly biological functionality.

SUMMARY

In one embodiment, a multilayer film comprises two or more layers of polyelectrolytes, wherein adjacent layers comprise oppositely charged polyelectrolytes, wherein a first layer polyelectrolyte comprises a first layer polypeptide comprising one or more first amino acid sequence motifs, wherein the one or more first amino acid sequence motifs consists of 5 to 15 amino acids and has a net charge per residue of 0.4. The first layer polypeptide is at least 15 amino acids long, and has a balance of charge at pH 7 greater than or equal to approximately one-half of the total length of the first layer polypeptide; wherein the first layer polypeptide comprises a therapeutic agent reversibly linked to the first layer polypeptide. A second layer comprises a second layer polyelectrolyte comprising a polycationic material or a polyanionic material having a molecular weight of greater than 1,000 and at least 5 charges per molecule, wherein the second layer does not comprise a polypeptide.

A method of controllably releasing a therapeutic agent from a polypeptide multilayer film, comprises providing the polypeptide multilayer film described above, and contacting the film with a stimulus suitable to stimulate release of the therapeutic agent from the reversible linkage.

In another embodiment, a method of assembling a polypeptide multilayer film comprises disposing a second layer polyelectrolyte onto a substrate, wherein the second layer polyelectrolyte comprising a polycationic material or a polyanionic material having a molecular weight of greater than 1,000 and at least 5 charges per molecule, wherein the second layer does not comprise a polypeptide; and disposing a first layer polypeptide on the second layer polyelectrolyte, wherein the first layer polypeptide comprises one or more first amino acid sequence motifs, wherein the one or more first amino acid sequence motifs consists of 5 to 15 amino acids and has a net charge per residue of 0.4. The first layer polypeptide is at least 15 amino acids long, and has a balance of charge at pH 7 greater than or equal to approximately one-half of the total length of the first layer polypeptide; and the first layer polypeptide comprises a therapeutic agent reversibly linked to the first layer polypeptide.

DETAILED DESCRIPTION

Figure 1:
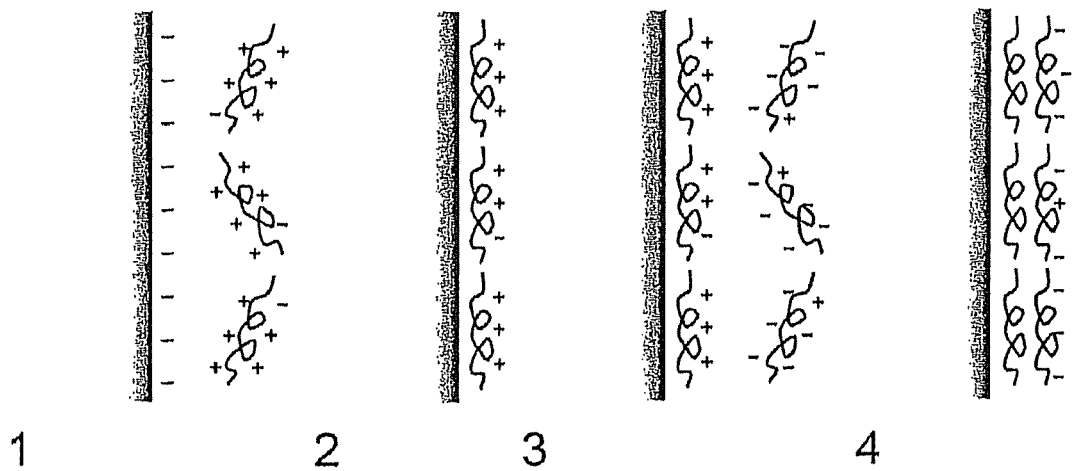
FIG. 1 shows a schematic of the assembly of oppositely charged polypeptides.
Figure 1:
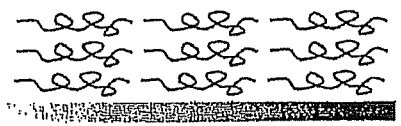
Figure 1:
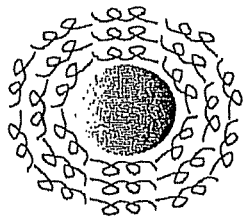

The present invention is directed to polypeptide multilayer films comprising at least one layer comprising a first layer polypeptide, wherein the polypeptide comprises a reversibly attached therapeutic agent, e.g., a drug. Polyelectrolyte multilayer coatings could be useful for drug delivery, for example, from medical implants such as a stent. In one approach, therapeutic agents are loaded into the coating after coating preparation, and the therapeutic agent is released by diffusion. In another approach, therapeutic agents are encapsulated within a multilayer coating; again, release is governed by diffusion. An alternative approach, disclosed herein, is to form a covalent link between the therapeutic agent and the first layer polypeptide, where the covalent link is reversible under some physiological conditions. For example, model thiol-bearing molecules of 5,5'-dithio-bis(2-nitrobenzoic acid) (DTNB) can be "loaded" onto Cys-containing 32-mer polypeptides by disulfide bond formation, the "loaded" peptides can be incorporated into a multilayer film by ELBL, and 2-nitro-5-thiobenzoate dianions (TNB) can be released from the film by a change in the redox potential of the surrounding liquid medium. Such loading and releasing has been demonstrated experimentally. DTNB, also known as Ellman's reagent, can be used to quantify free sulfhydryl groups and disulfides in peptides and proteins. An increase in the reducing potential of the surrounding liquid medium models passage of a coated particle from outside a living biological cell, where the environment is oxidizing, to inside, where it is reducing. The approach disclosed herein thus enables environmentally-stimulated release of a therapeutic agent which is covalently bound to a multilayer film by means of a disulfide bond, which is sensitive to the local redox potential.

In one embodiment, a multilayer film comprises two or more layers of polyelectrolytes, wherein adjacent layers comprise oppositely charged polyelectrolytes, wherein a first layer polyelectrolyte comprises a first layer polypeptide comprising one or more first amino acid sequence motifs, wherein the one or more first amino acid sequence motifs consists of 5 to 15 amino acids and has a net charge per residue of 0.4, wherein the first layer polypeptide is not a homopolymer, is at least 15 amino acids long, and has a balance of charge at pH 7 greater than or equal to approximately one-half of the total length of the first layer polypeptide. A second layer comprises a second layer polyelectrolyte comprising a polycationic material or a polyanionic material having a molecular weight of greater than 1,000 and at least 5 charges per molecule, wherein the second layer does not comprise a polypeptide. In one embodiment wherein the film comprises a substrate, the first layer polypeptide is the outermost, or solvent exposed layer, that is, the furthest layer from the substrate.

Also disclosed herein are methods of release of a therapeutic agent from a polypeptide multilayer film.

As used herein, "layer" means a thickness increment, e.g., on a substrate for film formation, following an adsorption step. "Multilayer" means multiple (i.e., two or more) thickness increments. A "polyelectrolyte multilayer film" is a film comprising one or more thickness increments of polyelectrolytes. After deposition, the layers of a multilayer film may not remain as discrete layers. In fact, it is possible that there is significant intermingling of species, particularly at the interfaces of the thickness increments.

The term "polyelectrolyte" includes polycationic and polyanionic materials having a molecular weight of greater than 1,000 and at least 5 charges per molecule. Suitable polycationic materials include, for example, polyamines. Polyamines include, for example, a polypeptide, polyvinyl amine, poly(aminostyrene), poly(aminoacrylate), poly(N-methyl aminoacrylate), poly(N-ethylaminoacrylate), poly(N,N-dimethyl aminoacrylate), poly(N,N-diethylaminoacrylate), poly(aminomethacrylate), poly(N-methyl aminomethacrylate), poly(N-ethyl aminomethacrylate), poly(N,N-dimethyl aminomethacrylate), poly(N,N-diethyl aminomethacrylate), poly(ethyleneimine), poly(diallyldimethylammonium chloride), poly(N,N,N-trimethylaminoacrylate chloride), poly(methyacrylamidopropyltrimethyl ammonium chloride), chitosan and combinations comprising one or more of the foregoing polycationic materials. Suitable polyanionic materials include, for example, a polypeptide, a nucleic acid, alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose, acidic polysaccharides, and croscarmellose, synthetic polymers and copolymers containing pendant carboxyl groups, and combinations comprising one or more of the foregoing polyanionic materials.

"Amino acid" means a building block of a polypeptide. As used herein, "amino acid" includes the 20 common naturally occurring L-amino acids, all other natural amino acids, all non-natural amino acids, and all amino acid mimics, e.g., peptoids.

"Naturally occurring amino acids" means the 20 common naturally occurring L-amino acids, that is, glycine, alanine, valine, leucine, isoleucine, serine, threonine, cysteine, methionine, aspartic acid, asparagine, glutamic acid, glutamine, arginine, lysine, histidine, phenylalanine, tyrosine, tryptophan, and proline.

"Non-natural amino acid" means an amino acid other than any of the 20 common naturally occurring L-amino acids. A non-natural amino acid can have either L- or D-stereochemistry.

"Peptoid," or N-substituted glycine, means an analog of the corresponding amino acid monomer, with the same side chain as the corresponding amino acid but with the side chain appended to the nitrogen atom of the amino group rather than to the $\alpha$-carbons of the residue. Consequently, the chemical linkages between monomers in a polypeptoid are not peptide bonds, which can be useful for limiting proteolytic digestion.

"Amino acid sequence" and "sequence" mean a contiguous length of polypeptide chain that is at least two amino acid residues long.

"Residue" means an amino acid in a polymer or oligomer; it is the residue of the amino acid monomer from which the polymer was formed. Polypeptide synthesis involves dehydration, that is, a single water molecule is "lost" on addition of the amino acid to a polypeptide chain.

"Amino acid sequence motif" means a contiguous amino acid sequence comprising n residues, wherein n is 5 to 15. In one embodiment, the magnitude of the net charge per residue of an amino acid sequence motif is greater than or equal to 0.4. In another embodiment, the magnitude of the net charge per residue of an amino acid sequence motif is greater than or equal to 0.5. As used herein, the magnitude of the net charge refers to the absolute value of the net charge, that is, the net charge can be positive of negative.

"Designed polypeptide" means a polypeptide comprising one or more amino acid sequence motifs, wherein the polypeptide is at least 15 amino acids in length and the ratio of the number of charged residues of the same polarity minus the number of residues of the opposite polarity to the total number of residues in the polypeptide is greater than or equal to 0.4 at pH 7.0. In other words, the magnitude of the net charge per residue of the polypeptide is greater than or equal to 0.4. In one embodiment, the ratio of the number of charged residues of the same polarity minus the number of residues of the opposite polarity to the total number of residues in the polypeptide is greater than or equal to 0.5 at pH 7.0. In other words, the magnitude of the net charge per residue of the polypeptide is greater than or equal to 0.5. While there is no absolute upper limit on the length of the polypeptide, in general, designed polypeptides suitable for ELBL deposition have a practical upper length limit of 1,000 residues.

"Primary structure" means the contiguous linear sequence of amino acids in a polypeptide chain, and "secondary structure" means the more or less regular types of structure in a polypeptide chain stabilized by non-covalent interactions, usually hydrogen bonds. Examples of secondary structure include α-helix, β-sheet, and β-turn.

"Polypeptide multilayer film" means a film comprising one or more polypeptides such as the designed polypeptides defined above. For example, a polypeptide multilayer film comprises a first layer comprising a designed polypeptide and a second layer comprising a polyelectrolyte have a net charge of opposite polarity to the designed polypeptide. For example, if the first layer has a net positive charge, the second layer has a net negative charge; and if the first layer has a net negative charge, the second layer has a net positive charge. The second layer comprises another designed polypeptide or another polyelectrolyte.

"Substrate" means a solid material with a suitable surface for adsorption of polyelectrolytes from aqueous solution. The surface of a substrate can have essentially any shape, for example, planar, spherical, rod-shaped, and the like. Substrate surface are regular or irregular. A substrate can be a crystal. A substrate optionally includes bioactive molecules. Substrates range in size from the nanoscale to the macroscale. Moreover, a substrate optionally comprises several small sub-particles. A substrate can be made of organic material, inorganic material, bioactive material, or a combination thereof. Nonlimiting examples of substrates include silicon wafers; charged colloidal particles, e.g., microparticles of $CaCO_3$ or of melamine formaldehyde; protein crystals; nucleic acid crystals; biological cells such as erythrocytes, hepatocytes, bacterial cells, or yeast cells; organic polymer lattices, e.g., polystyrene or styrene copolymer lattices; liposomes; organelles; and viruses. In one embodiment, a substrate is a medical device such as an artificial pacemaker, a cochlear implant, or a stent.

When a substrate is disintegrated or otherwise removed during or after film formation, it is called "a template" (for film formation). Template particles can be dissolved in appropriate solvents or removed by thermal treatment. If, for example, partially cross-linked melamine formaldehyde template particles are used, the template can be disintegrated by mild chemical methods, e.g., in DMSO, or by a change in pH value. After dissolution of the template particles, hollow multilayer shells remain which are composed of alternating polyelectrolyte layers.

A "microcapsule" is a polyelectrolyte film in the form of a hollow shell or a coating surrounding a core. The core comprises a variety of different encapsulants, such as, a protein, a drug, or a combination thereof, in liquid or crystalline form, for example.

"Bioactive molecule" means a molecule, macromolecule, or macromolecular assembly having a biological effect. The specific biological effect can be measured in a suitable assay and normalizing per unit weight or per molecule of the bioactive molecule. A bioactive molecule can be encapsulated, retained behind, or encapsulated within a polyelectrolyte film. Nonlimiting examples of a bioactive molecule are a drug, a crystal of a drug, a protein, a functional fragment of a protein, a complex of proteins, a lipoprotein, an oligopeptide, an oligonucleotide, a nucleic acid, a ribosome, an active therapeutic agent, a phospholipid, a polysaccharide, a lipopolysaccharide. As used herein, "bioactive molecule" further encompasses biologically active structures, such as, for example, a functional membrane fragment, a membrane structure, a virus, a pathogen, a cell, an aggregate of cells, and an organelle. Examples of a protein that can be encapsulated or retained behind a polypeptide film are hemoglobin; enzymes, such as for example glucose oxidase, urease, lysozyme and the like; extracellular matrix proteins, for example, fibronectin, laminin, vitronectin and collagen; and an antibody. Examples of a cell that can be encapsulated or retained behind a polyelectrolyte film is a transplanted islet cell, a eukaryotic cell, a bacterial cell, a plant cell, and a yeast cell.

Therapeutic agents are a subset of bioactive molecules. "Therapeutic agent" means a compound, element, or mixture that when administered to a patient, alone or in combination with another compound, element, or mixture, confers, directly or indirectly, a physiological effect on the patient. The indirect physiological effect may occur via a metabolite or other indirect mechanism. When the active agent is a compound, then salts, solvates (including hydrates) of the free compound or salt, crystalline forms, non-crystalline forms, and any polymorphs of the compound are contemplated herein.

Suitable therapeutic agents are anti-inflammatory substances, coronary vasodilators, cerebral vasodilators, peripheral vasodilators, anti-infectives, psychotropics, antimanics, stimulants, anti-histamines, gastro-intestinal sedatives, antidiarrheal preparations, anti-anginal drugs, vasodilators, antiarrythmics, anti-hypertensive drugs, vasoconstrictors, drugs useful to treat migraines, anticoagulants and antithrombotic drugs, analgesics, anti-pyretics, hypnotics, sedatives, antiemetics, anti-nauseants, anticonvulsants, neuromuscular drugs, hyper- and hypoglycaemic agents, thyroid and antithyroid preparations, diuretics, antipasmodics, uterine relaxants, mineral and nutritional additives, antiobesity drugs, anabolic drugs, erythropoietic drugs, antiasthmatics, expectorants, cough suppressants, mucolytics, antiuricemic drugs, other drugs, and combinations comprising one or more of the foregoing therapeutic agents.

"Biocompatible" means causing no substantial adverse health effect upon oral ingestion, topical application, transdermal application, subcutaneous injection, intramuscular injection, inhalation, implantation, or intravenous injection. For example, biocompatible films include those that do not cause a substantial immune response when in contact with the immune system of, for example, a human being.

"Immune response" means the response of the cellular or humoral immune system to the presence of a substance anywhere in the body. An immune response can be characterized in a number of ways, for example, by an increase in the bloodstream of the number of antibodies that recognize a certain antigen. Antibodies are proteins secreted by B cells, and an antigen is an entity that elicits an immune response. The human body fights infection and inhibits reinfection by increasing the number of antibodies in the bloodstream and elsewhere. The specific immune response depends somewhat on the individual, though general patterns of response are the norm.

"Epitope" means the structure or sequence of a protein that is recognized by an antibody. Ordinarily an epitope will be on the surface of a protein. A "continuous epitope" is one that involves several contiguous amino acid residues, not one that involves amino acid residues that happen to be in contact or in the limited region of space in a folded protein.

The present invention is directed to polypeptide multilayer films comprising a first layer polypeptide, wherein the first layer polypeptide comprises a reversibly attached bioactive molecule. Other layers comprise designed polypeptides or other polycations or polyanions.

The design principles for polypeptides suitable for electrostatic layer-by-layer deposition are elucidated in U.S. Patent Publication No. 2005/0069950, incorporated herein by reference. Briefly, the primary design concerns are the length and charge of the polypeptide. Electrostatics is the most important design concern because it is the basis of ELBL. Without suitable charge properties, a polypeptide will not be substantially soluble in aqueous solution at pH 4 to 10 and cannot readily be used for the fabrication of a multilayer film by ELBL. Other design concerns include the physical structure of the polypeptides, the physical stability of the films formed from the polypeptides, and the biocompatibility and bioactivity of the films and the constituent polypeptides.

As defined above, a designed polypeptide means a polypeptide comprising one or more amino acid sequence motifs, wherein the polypeptide is at least 15 amino acid residues in length and the magnitude of the net charge per residue of the polypeptide is greater than or equal to 0.4 at pH 7.0. "Amino acid sequence motif" means a contiguous amino acid sequence comprising n amino acid residues, wherein n is 5 to 15. Positively-charged (basic) naturally-occurring amino acids at pH 7.0 are Arg, His, and Lys. Negatively-charged (acidic) naturally-occurring amino acid residues at pH 7.0 are Glu and Asp. An amino acid motif comprising a mixture of amino acid residues of opposite charge can be employed so long as the overall ratio of charge meets the specified criteria. In one embodiment, a designed polypeptide is not a homopolymer.

In one exemplary embodiment, the amino acid sequence motif comprises 7 amino acid residues. Four charged amino acids is a suitable minimum for a motif size of 7, because fewer than 4 charges yields decreased peptide solubility and decreased control over ELBL. Further, regarding biocompatibility, each identified amino acid sequence motif in genomic data is long enough at 7 amino acid residues to constitute a continuous epitope, but not so long as to correspond substantially to residues both on the surface of a protein and in its interior. Thus, the charge and length of the amino acid sequence motif help to ensure that an amino acid sequence motif identified in genomic data is likely to occur on the surface of the folded protein from which the sequence motif is derived. In contrast, a very short motif could appear to the body to be a random sequence, or one not specifically "self," and therefore elicit an immune response.

In some cases, a design concern regarding amino acid sequence motifs and designed polypeptides is their propensity to form secondary structures, notably α-helix or β-sheet. In some embodiments, it is desirable to be able to control, e.g., minimize, secondary structure formation by the designed polypeptides in an aqueous medium in order to maximize control over thin film layer formation. First, it is preferred that sequence motifs be relatively short, that is about 5 to about 15 amino acid residues, because long motifs are more likely to adopt a stable three-dimensional structure in solution. Second, a linker, such as a glycine or proline residue, covalently joined between successive amino acid sequence motifs in a designed polypeptide will reduce the propensity of the polypeptide to adopt secondary structure in solution. Glycine, for example, has a very low α-helix propensity and a very low β-sheet propensity, making it energetically very unfavorable for a glycine and its neighboring amino acids to form regular secondary structure in aqueous solution. Third, the α-helix and β-sheet propensity of the designed polypeptides themselves can be minimized by selecting amino acid sequence motifs for which the summed α-helix propensity is less than 7.5 and the summed β-sheet propensity is less than 8. "Summed" propensity means the sum of the α-helix or β-sheet propensities of all amino acids in a motif. Amino acid sequence motifs having a somewhat higher summed α-helix propensity and/or summed β-sheet propensity are suitable for ELBL, particularly when joined by linkers such as Gly or Pro. In certain applications, the propensity of a polypeptide to form secondary structure can be relatively high as a specific design feature of thin film fabrication. The secondary structure propensities for all 20 naturally occurring amino acids can be calculated using the method of Chou and Fasman (see P. Chou and G. Fasman, Biochemistry, 13:211 (1974), which is incorporated by reference herein in its entirety).

Another design concern is control of the stability of polypeptide ELBL films. Ionic bonds, hydrogen bonds, van der Waals interactions, and hydrophobic interactions contribute to the stability of multilayer films. In addition, covalent disulfide bonds formed between sulfhydryl-containing amino acids in the polypeptides within the same layer or in adjacent layers can increase structural strength. Sulfydryl-containing amino acids include cysteine and homocysteine. In addition, a sulfhydryl can be added to β-amino acids such as D,L-β-amino-β-cyclohexyl propionic acid; D,L-3-aminobutanoic acid; or 5-(methylthio)-3-aminopentanoic acid. Sulfhydryl-containing amino acids can be used to "lock" (bond together) and "unlock" layers of a multilayer polypeptide film by a change in oxidation potential. Also, the incorporation of a sulfhydryl-containing amino acid in a sequence motif of a designed polypeptide enables the use of relatively short peptides in thin film fabrication, by virtue of intermolecular disulfide bond formation. Amino acid sequence motifs containing sulfhydryl-containing amino acids may be selected from a library of motifs identified using the methods described below, or designed de novo.

In one embodiment, the designed sulfhydryl-containing polypeptides, whether synthesized chemically or produced in a host organism, are assembled by ELBL in the presence of a reducing agent to prevent premature disulfide bond formation. Following film assembly, the reducing agent is removed and an oxidizing agent is added. In the presence of the oxidizing agent disulfide bonds form between sulfhydryls groups, thereby "locking" together the polypeptides within layers and between layers where thiol groups are present. Suitable reducing agents include dithiothreitol ("DTT"), 2-mercaptoethanol (2-ME), reduced glutathione, tris(2-carboxyethyl)phosphine hydrochloride (TCEP), and combinations of more than one of these chemicals. Suitable oxidizing agents include oxidized glutathione, tert-butylhydroperoxide (t-BHP), thimerosal, diamide, 5,5'-dithio-bis-(2-nitro-benzoic acid) (DTNB), 4,4'-dithiodipyridine, sodium bromate, hydrogen peroxide, sodium tetrathionate, porphyrindin, sodium orthoiodosobenzoate, and combinations of more than one of these chemicals.

Biocompatibility is a design concern in biomedical applications. In such applications, genomic or proteomic information is used as a basis for polymer design to yield, ideally, "immune inert" polypeptides. The approach will be particularly useful if the fabricated or coated object will make contact with circulating blood. Because the amino acid sequence motifs are highly polar, they typically occur on the surface of the native folded form of the protein from which they are derived. The "surface" is that part of a folded protein that is in contact with the solvent or inaccessible to the solvent solely because of the granular nature of water. Amino acid sequence motifs identified in blood proteins are effectively always in contact with cells and molecules of the immune system while the protein is in the blood. Therefore, polypeptides derived from the surface of folded blood proteins are less likely to be immunogenic than sequences selected at random. Designed polypeptides will generally be biocompatible, but the extent of immune response or any other type of biological response may well depend on specific details of a sequence motif.

Bioactivity can be incorporated into a film, coating or microcapsule by a number of methods. For example, a designed polypeptide comprising the film can comprise a functional domain. Alternatively, bioactivity may be associated with another bioactive molecule encapsulated or coated by the polypeptide thin film. In one embodiment, the template comprises a bioactive molecule such as a protein crystal.

A functional domain in this context is an independently thermostable region of a protein that has specific biofunctionality (e.g., binding phosphotyrosine). In a multi-domain protein, multiple functional domains may exist, as for example in the protein tensin, which encompasses a phosphotyrosine binding domain and a protein tyrosine phosphatase domain. The inclusion of a functional domain in a designed polypeptide incorporated into a multilayer film can provide the film with a desired functionality, including, for example, specific ligand binding, targeting in vivo, biosensing, and biocatalysis.

The bioactive molecule can be a protein, a functional fragment of a protein, a functional fragment of a protein that is not part of a designed polypeptide, a complex of proteins, an oligopeptide, an oligonucleotide, a nucleic acid, a ribosome, an active therapeutic agent, a phospholipid, a polysaccharide, a lipopolysaccharide, a functional membrane fragment, a membrane structure, a virus, a pathogen, a cell, an aggregate of cells, an organelle, a lipid, a carbohydrate, a pharmaceutical, or an antimicrobial agent. The bioactive molecule can be in the form of a well-ordered or amorphous crystal. The protein can be an enzyme or an antibody. The substrate can comprise the bioactive molecule. In one embodiment, the substrate has a bioactive molecule disposed on its surface prior to deposition of layers of oppositely charged polypeptides. In another embodiment, the substrate is a crystal comprising the bioactive molecule.

In one embodiment, amino acid sequence motifs are designed de novo. In other embodiments, amino acid sequence motifs are selected from the genomic or proteomic information of a specific organism, such as the human genome. For example, the primary structure of complement C3 (gi168766) or lactotransferrin (gi/4505043) can be used to search for amino acid sequence motifs in a human blood protein.

A method of identifying a first amino acid sequence motif in a polypeptide comprises selecting a starter amino acid residue in the polypeptide; examining an amino acid sequence comprising the starter amino acid residue and the following n–1 amino acid residues in the polypeptide for occurrences of positive and negative charges, wherein n is 5 to 15; determining the 5-15 amino acid residues as an amino acid sequence motif if the net charge of the side chains of the 5-15 amino acid residues at pH 7 is greater than or equal to 0.4*n; or discarding the sequence if the net charge of the side chains of the 5-15 amino acid residues at pH 7 is less than 0.4*n.

In one embodiment, the process of searching protein sequence data for a negatively charged amino acid sequence motif of length n comprising only amino acids that are neutral or negatively charged is described as follows. First, a first amino acid residue is selected in a protein sequence. Second, this amino acid residue and the following n–1 amino acid residues are examined for occurrences of arginine (Arg), histidine (His), or lysine (Lys) (the three naturally occurring amino acids that may be positively charged at neutral pH), where n is 5 to 15. Third, if one or more Arg, His, or Lys residues is found in these n amino acid residues, the process is begun anew at a second amino acid residue. If, however, no Arg, His, or Lys is found in these n residues, the n residues are examined to determine the number of occurrences of glutamate (Glu) and/or aspartate (Asp) (the two negatively charged amino acids at neutral pH). Fourth, if there are at least 0.4*n occurrences of Glu and/or Asp in the n residues, the sequence is cataloged as a negatively charged amino acid sequence motif. If, however, fewer than 0.4*n occurrences of negatively charged amino acid residues are found, the sequence beginning with the first amino acid residue is discarded and the process is begun anew, for example, at a second amino acid residue immediately adjacent to the first amino acid residue. After cataloging a motif, the process can begin anew at a second amino acid residue.

The process for identifying a positively charged sequence motif is analogous to searching protein sequence data for an n residue-long amino acid sequence comprising only amino acid residues that are neutral or positively charged, and for which the magnitude of the net charge of the amino acid residue side chains at neutral pH is greater than or equal to 0.4*n.

Also analogous is the process for identifying a negatively charged amino acid sequence motif or a positively charged amino acid sequence motif of length n, allowing both positively and negatively charged amino acid residues in the motif. For example, the procedure for identifying a positively charged amino acid sequence motif of length n would be to select a first amino acid residue in a polypeptide. Next, examine this amino acid residue and the following n–1 amino acid residues for occurrences of residues that are positively or negatively charged at pH 7. Determine the net charge of the n amino acid residue side chains. If the absolute value of the net charge is less than 0.4*n, then the sequence is discarded and a new search is begun at another amino acid, while if the absolute value of the net charge is greater than or equal to 0.4*n, then the sequence is an amino acid sequence motif The motif will be positive if net charge is greater than zero and negative if the net charge is less than zero.

De novo design of amino acid sequence motifs as presently defined follows essentially similar rules, except that the sequences are not limited to those found in nature. A length of motif n and a desired sign and magnitude of net charge are chosen. Then, n amino acids are selected for the amino acid sequence motif that result in the desired sign and magnitude of charge, so that the absolute value of the net charge of the n amino acids is greater than or equal to 0.4*n. A potential advantage of de novo design of an amino acid sequence motif is that the practitioner can select from among all amino acids (the 20 naturally occurring ones and all non-natural amino acids) to achieve the desired net charge, rather than being limited to the amino acids found in a particular known protein sequence. The larger pool of amino acids enlarges the potential range of physical, chemical and/or biological characteristics that can be selected in designing the sequence of the motif compared to identification of an amino acid sequence motif in a genomic sequence.

De novo design of amino acid sequence motifs as presently defined follows essentially similar rules, except that the sequences are not limited to those found in nature. A length of motif n and a desired sign and magnitude of net charge are chosen. Then, n amino acids are selected for the amino acid sequence motif that result in the desired sign and magnitude of charge, so that the absolute value of the net charge of the n amino acids is greater than or equal to 0.4*n. A potential advantage of de novo design of an amino acid sequence motif is that the practitioner can select from among all amino acids (the 20 naturally occurring ones and all non-natural amino acids) to achieve the desired net charge, rather than being limited to the amino acids found in a particular known protein sequence. The larger pool of amino acids enlarges the potential range of physical, chemical and/or biological characteristics that can be selected in designing the sequence of the motif compared to identification of an amino acid sequence motif in a genomic sequence.

A designed polypeptide as presently defined will comprise one or more amino acid sequence motifs. The same motif may be repeated, or different motifs may be joined in designing a polypeptide for ELBL. In one embodiment, the amino acid sequence motifs are covalently joined with no intervening sequence. In another embodiment, a designed polypeptide comprises two or more amino acid sequence motifs covalently joined by a linker. The linker can be amino acid based, e.g., one or more amino acid residues such as glycine or proline, or it can be any other compound suitable for covalently linking two amino acid sequence motifs. In one embodiment, a linker comprises 1-4 amino acid residues, for example, 1-4 glycine and/or proline resides. The linker comprises a suitable length or composition so that the designed polypeptide is maintained at a magnitude of net charge per residue that is greater than or equal to 0.4.

In one embodiment, a designed polypeptide is greater than or equal to 15 amino acid residues long. In other embodiments, a designed polypeptide is greater than 18, 20, 25, 30, 32 or 35 amino acids long. 1,000 residues is a practical upper bound on polypeptide length.

Once amino acid sequence motifs have been selected or designed de novo, a designed polypeptide with amino acid-based linkers is synthesized using methods well known in the art, such as solid phase synthesis and F-moc chemistry, or heterologous expression in bacteria following gene cloning and transformation. Designed polypeptides may be synthesized by a peptide synthesis company, for example, Global Peptide (Ft Collins, Colo.), produced in the laboratory using a peptide synthesizer, or produced by recombinant DNA methods. Any development of novel methods of peptide synthesis could enhance the production of peptides but would not fundamentally change peptide design as described herein.

After synthesis, the first layer polypeptide is reversibly linked to a therapeutic agent. Reversible linking includes both covalent and non-covalent bonding, so long as the therapeutic agent is released from the first layer polypeptide upon exposure to a suitable stimulus. The therapeutic agent can be linked to the N-terminus, the C-terminus, or to the side chain of the polypeptide, either as found in nature or chemically modified to facilitate attachment and release. Covalent reversible linkages can be formed, for example, between a drug and free sulfhydryl groups, free amino groups, and free carboxyl groups on the first layer polypeptide. Non-covalent reversible linkages include, for example, ionic bonds and hydrophobic interactions.

In one embodiment, an alcohol, amine or carboxylic acid group of the therapeutic agent is covalently attached to the N-terminus, the C-terminus or the side chain of the peptide. The location of attachment depends on the choice of functional group. For example, if the therapeutic agent is a carboxylic acid (e.g., aspirin) then the N-terminus of the peptide is a suitable point of attachment. If the therapeutic agent is an amine (e.g., ampicillin), then the C-terminus is a suitable point of attachment in order to achieve a stable peptide linked active agent. In both the C- and N-terminus examples, one monomeric unit forming a new peptide bond in essence, adds a molecule to the end of the peptide.

If the therapeutic agent is an amine, an alternate method of attaching the amine to the C-terminus of the peptide is to allow the amine to initiate attachment. If the therapeutic agent is an alcohol, then either the C-terminus or the N-terminus is a suitable point of attachment in order to achieve a stable composition. For example, when the therapeutic agent is an alcohol, the alcohol can be converted into an alkylchloroformate with phosgene or triphosgene. This intermediate is then reacted with the N-terminus of the peptide to produce a therapeutic agent peptide composition linked via a carbamate. The carbamate therapeutic agent may then be released from the peptide by intestinal peptidases, amidases, or esterases.

Alternatively, an alcohol therapeutic agent can be selectively bound to the gamma carboxylate of glutamic acid and then this conjugate covalently attached to the C-terminus of the peptide. Because the glutamic acid-therapeutic agent conjugate can be considered a dimer, this product adds two monomeric units to the C-terminus of the peptide where the glutamic acid moiety serves as a spacer between the peptide and the therapeutic agent. Intestinal enzymatic hydrolysis of the key peptide bond releases the glutamic acid-drug moiety from the peptide carrier. The newly formed free amine of the glutamic acid residue will then undergo an intramolecular transamination reaction, thereby, releasing the therapeutic agent with coincident formation of pryoglutamic acid If the therapeutic agent is a ketone or an aldehyde, then a ketal is formed with a linker that has a pendant group suitable for attachment to the N-terminus, C-terminus or side chain of the peptide. For example, a ketal can be formed by the reaction of methyltribofuranoside or glucose with methylnaltrexone as shown in example of glucose reacting with methylnaltrexone. The remaining free hydroxyl from the sugar moiety can then be treated as an alcohol for attachment to the C-terminus or a suitable side chain of the peptide.

In one embodiment, the therapeutic agent is attached to the N-terminus of the peptide. Suitable amino acids for attachment include glutamic acid, aspartic acid, serine, and lysine, for example. Suitable drugs for N-terminal attachment typically provide a carboxylic acid or an inorganic functional group for conjugation such as, for example, ibuprofen, furosemide, gemfibrozil, and naproxen.

In one embodiment, the therapeutic agent is attached to the C-terminus of the peptide. The C-terminus attachment of a therapeutic agent to a peptide can be formed through a plurality of active agent functional groups. The functional groups include amines and their equivalents and alcohols and their equivalents. While any amino acid may be used to connect the active agent to the C-terminus, glutamic acid, aspartic acid, serine and lysine are particularly suitable amino acids. Suitable active agents for C-terminal attachment are active agents with alcohol and amino functional groups such as, for example, atenolol, metropolol, propanolol, methylphenidate and sertraline.

In one embodiment, the therapeutic agent is covalently attached to the side chains of the polypeptide. A carboxylic acid-containing active agent can be attached to the amine or alcohol group of the peptide side chain to form an amide or ester, respectively. An amine containing active agent can be attached to the carboxylate, carbamide or guanine group of the side chain to form an amide or a new guanine group. In addition, linkers can be selected from the group of all chemical classes of compounds such that virtually any side chain of the peptide can be attached.

In another embodiment, attachment of the therapeutic agent to the peptide is done via the incorporation of a linker between the active agent and the peptide. The linker should have a functional pendant group, such as a carboxylate, an alcohol, thiol, oxime, hydraxone, hydrazide, or an amine group, to covalently attach to the peptide. In one embodiment, the therapeutic agent is an alcohol and the alcohol group is covalently attached to the N-terminus of the peptide via a linker. In another embodiment, the therapeutic agent is a ketone or an aldehyde, which is attached to a linker through the formation of a ketal or acetal, respectively, and the linker has a pendant group that is attached to the peptide. In yet another embodiment, the therapeutic agent is an amide, an imide, an imidazole or a urea where the nitrogen is attached to the linker and the pendant group of the linker is attached to the peptide.

In one embodiment, the first layer polypeptide and the therapeutic agent each comprises a free sulfhydryl group. Suitable therapeutic agents naturally comprising free sulfhydryl groups include, for example, cysteamine, dimercaprol, sodium 2-mercaptoethane sulfonate, acetylcysteine, omapatrilat, captopril, and the like. In addition, a known therapeutic agent in which no free sulfhydryl group is present can be modified by chemical methods to contain a free sulfhydryl group.

A method of making a polyelectrolyte multilayer film comprises depositing a plurality of layers of oppositely charged polyelectrolytes on a substrate. Successively deposited polyelectrolytes have opposite net charges. In the present case, at least a first layer polyelectrolyte comprising a reversibly linked therapeutic agent is deposited. FIG. 1 is a schematic illustrating ELBL deposition. In one embodiment, deposition of a polyelectrolyte such as a designed polypeptide comprises exposing the substrate to an aqueous solution comprising a designed polypeptide (or other polyelectrolyte) at a pH at which it has a suitable net charge for ELBL. In other embodiments, the deposition of a designed polypeptide or other polyelectrolyte on the substrate is achieved by sequential spraying of solutions of oppositely charged polyelectrolytes. In yet other embodiments, deposition on the substrate is by simultaneous spraying of solutions of oppositely charged polyelectrolytes.

In the ELBL method of forming a multilayer film, the opposing charges of the adjacent layers provide the driving force for assembly. It is not critical that polyelectrolytes in opposing layers have the same net linear charge density, only that opposing layers have opposite charges. One standard film assembly procedure for deposition includes forming aqueous solutions of the polyelectrolytes at a pH at which they are ionized (i.e., pH 4-10), providing a substrate bearing a surface charge, and alternating immersion of the substrate into the charged polyelectrolyte solutions. The substrate is optionally washed in between deposition of alternating layers.

The concentration of polyelectrolyte suitable for deposition of the polyelectrolyte can readily be determined by one of ordinary skill in the art. An exemplary concentration is 0.1 to 10 mg/mL. Typically, the thickness of the layer produced is substantially independent of the solution concentration of the polyion during deposition in the stated range. For typical non-polypeptide polyelectrolytes such as poly(acrylic acid) and poly(allylamine hydrochloride), layer thicknesses are about 3 to about 5 Å, depending on the ionic strength of solution. Short polyelectrolytes often form thinner layers than long polyelectrolytes. Regarding film thickness, polyelectrolyte film thickness depends on humidity as well as the number of layers and composition of the film. For example, PLL/PLGA films 50 nm thick shrink to 1.6 nm upon drying with nitrogen. In general, films of 1 nm to 100 nm or more in thickness can be formed depending on the hydration state of the film and the molecular weight of the polyelectrolytes employed in the assembly.

In addition, the number of layers required to form a stable polyelectrolyte multilayer film will depend on the polyelectrolytes in the film. For films comprising only low molecular weight polypeptide layers, a film will typically have 4 or more bilayers of oppositely charged polypeptides. For films comprising high molecular weight polyelectrolytes such as poly (acrylic acid) and poly(allylamine hydrochloride), films comprising a single bilayer of oppositely charged polyelectrolyte can be stable.

In another embodiment, a method of releasing a therapeutic agent from a polypeptide multilayer film comprises providing a polypeptide multilayer film as described herein comprising a first layer polypeptide having reversibly linked thereto a therapeutic agent, and contacting the film with a stimulus suitable to stimulate release of the therapeutic agent from the reversible linkage and thus from the film.

In one embodiment, the therapeutic agent delivery is targeted into general systemic circulation. The pH environment of the bloodstream and/or alimentary tract can provide a suitable stimulus for release of the therapeutic agent. In another embodiment, the stimulus for release of the therapeutic agent from the peptide occurs by enzymatic action on the peptide-therapeutic agent conjugate in the bloodstream or by enzymatic action on the peptide-therapeutic agent conjugate in the alimentary tract followed by absorption through the intestines or stomach by the regular route of entry.

In one embodiment, the therapeutic agent is attached via a glutamic acid residue in the peptide. The complex is released from the peptide upon hydrolysis of the peptide and then the therapeutic agent is released from the glutamic acid by coincident intramolecular transamination. In another embodiment, the glutamic acid is replaced by aspartic acid, arginine, asparagine, cysteine, lysine, threonine, and serine, and wherein the therapeutic agent is attached to the side chain of the amino acid to form an amide, a thioester, an ester, an ether, a thioether, a carbonate, an anhydride, an orthoester, a hydroxamic acid, a hydrazone, sulfonamide, sulfonic esters, other derivatives of sulfur, or a carbamate. In yet another embodiment, the glutamic acid is replaced by a synthetic amino acid with a pendant group comprising an amine, an alcohol, a sulfhydryl, an amide, a urea, or an acid functionality, for example.

When the reversible linkage comprises an ionic bond, a suitable stimulus is a concentrated salt solution, e.g., 1 M NaCl. When the reversible linkage comprises a hydrophobic interaction, a suitable stimulus is a surfactant solution, e.g., 2% SDS. When the reversible linkage comprises a disulfide bond, suitable reducing agents to act as a stimulus for therapeutic agent release include dithiothreitol ("DTT"), 2-mercaptoethanol (2-ME), reduced glutathione, tris(2-carboxyethyl)phosphine hydrochloride (TCEP), and combinations of more than one of these chemicals.

The invention is further illustrated by the following non-limiting examples.

EXAMPLES

Materials and Methods

Materials: Peptides SEQ ID NO:1: $(KVKGKCKV)_3$ KVKGKCKY ("P1") and SEQ ID NO:2: $(EVEGECEV)_3$ EVEGECEY ("N1") (Genscript, Inc., USA) are oppositely charged at neutral pH due to protonation of lysine (K) and deprotonation of glutamic acid (E). The other amino acid residues are valine (V), glycine (G), and Cys (C). 4-15 kDa poly(L-lysine) ("PLL"), 13 kDa poly(L-glutamic acid) ("PLGA"), and DTNB were from Sigma (USA). DL-dithiothreitol (DTT), a reducing agent, was from Gold Biotechnology, Inc. (USA). All other reagents were from Sigma. P1, N1, PLL and PLGA were dissolved in TA buffer (10 mM tris (hydroxymethyl)aminomethane, 10 mM sodium acetate, 20 mM NaCl, 0.1% $NaN_3$, pH 7.4) to a concentration of 1 mg/mL.

Figure 2:
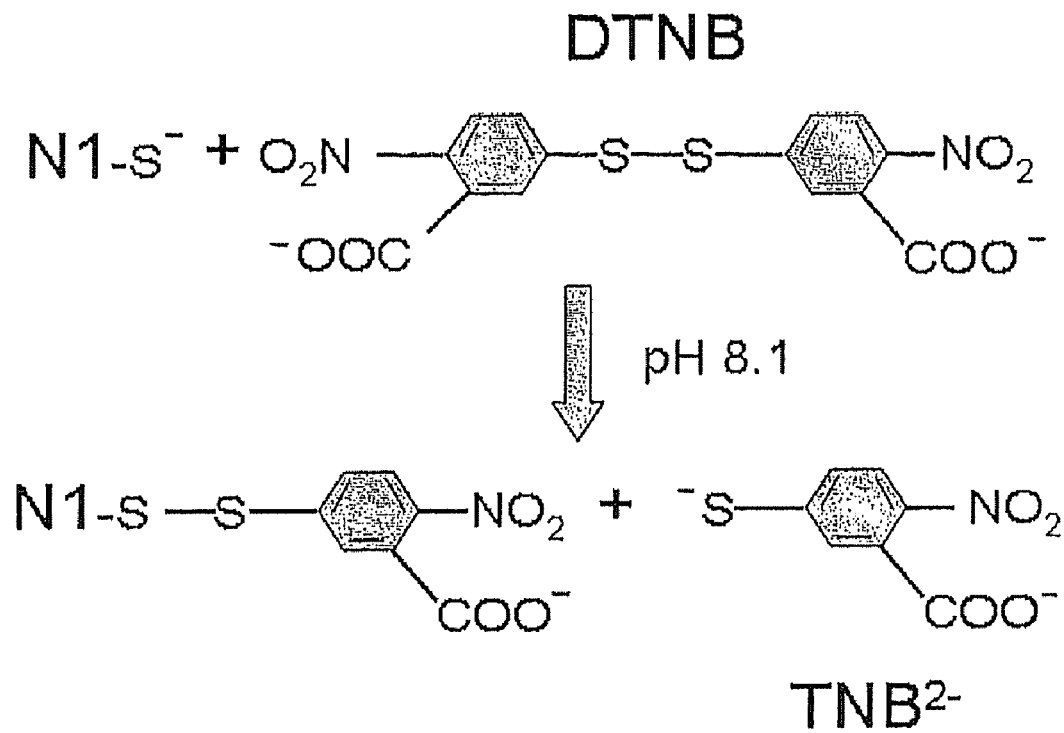
FIG. 2 shows the reaction of DTNB with Cys side chains in N1. A TNB group becomes attached to a peptide thiol group by formation of a disulfide bond.

Labeling of N1 with DTNB: Peptides P1 and N1 contain Cys residues. A free thiol group on a peptide will react with a DTNB molecule under oxidizing conditions (FIG. 2). In the process, a TNB molecule forms a mixed disulfide with a Cys side chain and a TNB molecule is released to the surroundings. An aqueous solution of free TNB is yellow and has an absorbance peak at 412 nm at mildly basic pH. The extinction coefficient of TNB ranges from 11,400 to 14,150 $M^{-1}$ $cm^{-1}$ depending on conditions.

Figure 6:
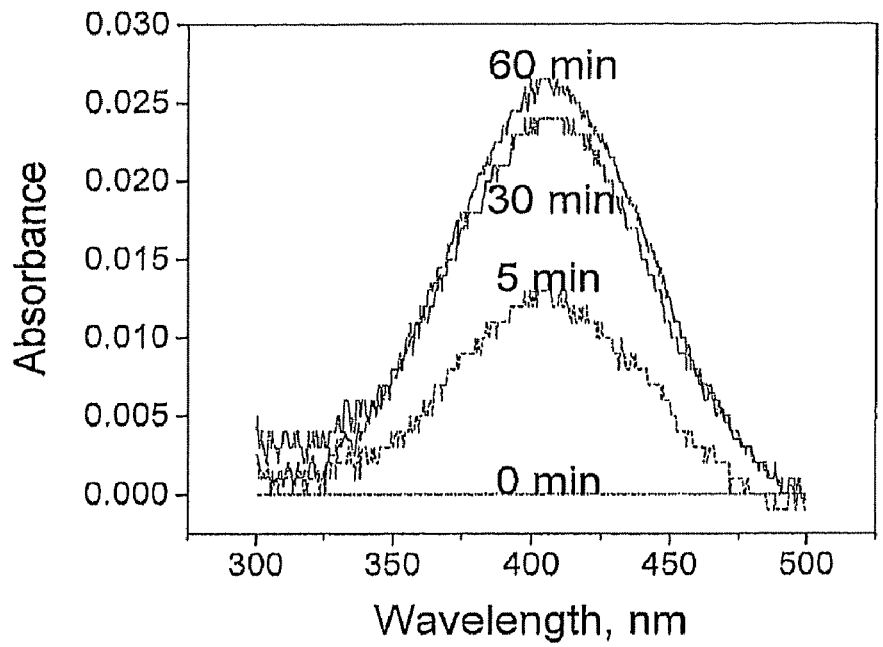
FIG. 6 shows absorbance spectra of liquid medium surrounding of 10 P1/LN1 nanocoatings, recorded 0, 5, 30, or 60 min after immersion in 0.1 mM DTT solution. TNB absorbance increases with time.

Lyophilized N1 was prepared for loading by dissolution of peptide in "reducing TA buffer" (TA buffer, 10 mM DTT, pH 8.1) and incubation at ambient temperature for 24 hours. 2 mL N1 solution was introduced into 1,000 MWCO dialysis tubing (SpectroPor® 7, Spectrum Laboratories, Inc., USA) and dialyzed against 200 mL "DTNB solution" (TA buffer, 10 mM DTNB, pH 8.1) with continuous stirring. The DTNB solution was changed after 1, 2, 4, and 17 hours. The dialysis bag containing labeled N1 (LN1) was then immersed in pH 7.4 TA buffer to remove excess DTNB and to shift the pH from 8.1 to 7.4. TA buffer was changed after 1, 2, 4, and 17 hours. The final concentration of LN1 was adjusted to 1 mg/mL with pH 7.4 TA buffer. UV absorbance spectra of LN1 before and after treatment with DTT are shown in FIG. 6.

Assembly of polypeptide multilayer nanocoatings: Polypeptide multilayer coatings were assembled on quartz microscope slides (Electron Microscopy Sciences, USA) after substrates were cleaned. A substrate was repetitively immersed in a positively charged polypeptide solution (P1 or PLL) and in a negatively charged polypeptide solution (N1, LN1, or PLGA) for 15 minutes per peptide adsorption step. Each peptide deposition step was followed by rinsing the coated slide in separate deionized water baths for 2 minutes, 1 minutes, and 1 minute. 30 layers of polypeptide were assembled in this way. In some cases, as indicated below, two "capping" bilayers of P1 and N1, symbolized as $(P1/N1)_2$, were assembled on top of 30-layer P1/LN1 coatings.

Figure 3:
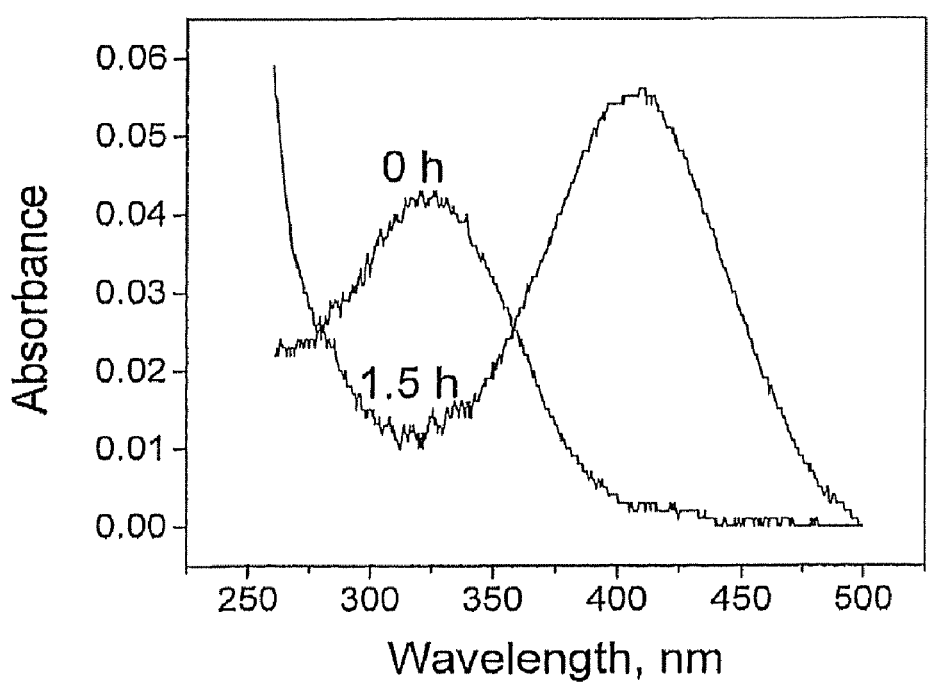
FIG. 3 shows the absorbance spectra of LN1 solutions after extensive dialysis to remove unreacted DTNB but before (0 h) and 1.5 h after adding DTT. The peak at 412 nm in the 1.5 h spectrum is due to TNB dianions, while that at 328 nm (0 h) is due to TNB-thiol mixed disulfide. The sharp increase in absorbance below 300 nm is due to DTT. The shoulder evident around 275 nm in later time points (not shown) is due to oxidized DTT.
Figure 4:
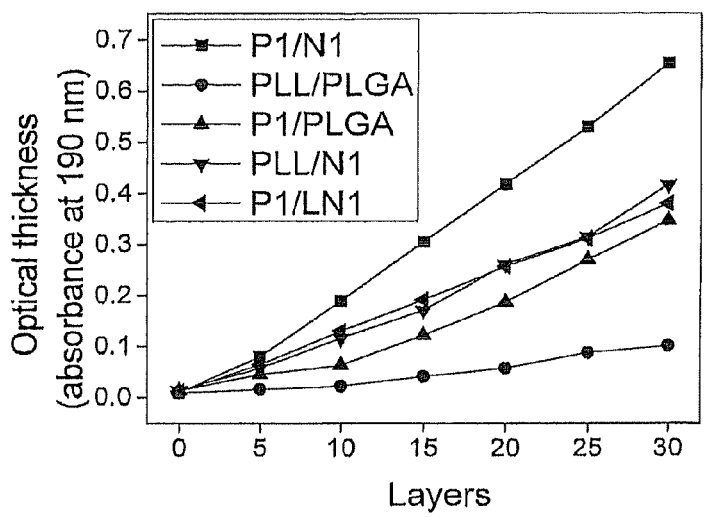
FIG. 4 shows multilayer film absorbance (optical thickness) at 190 nm v. number of layers.

Release of TNB from polypeptide multilayer nanocoatings: pH 7.4 LN1 solution was diluted 4-fold with deionized water, and DTT was added to a final concentration of 2 mM (FIG. 3). The mixture was gently agitated on a rocking platform throughout the TNB release process. Solution absorbance spectra were recorded with a Shimadzu UV mini 1240 UV-Vis spectrophotometer (Japan). The coating covered about 2 $cm^2$ of substrate in each case. The TNB absorbance peak was brought into the detectable range by immersing P1/LN1 coatings on 10 separate quartz plates in 3 mL release medium (pH 7.4 TA buffer diluted 4-fold with deionized water; 0, 0.1, or 1 mM DTT). The absorbance of the release medium was recorded by scanning spectrophotometry at defined time points. Each coating was immersed for 5 minutes for the first absorbance measurement and 15 minutes for subsequent measurements. The beaker containing the film sample and release medium was gently rocked throughout the release process.

Example 1

TNB Loading onto N1

DTT can maintain monothiols completely in the reduced state and reduce disulfides quantitatively. Polypeptide N1 was treated with DTT to break possible inter- and intramolecular disulfide bonds and to protect the free thiol groups of Cys residue side chains. The resulting N1 molecules, which have several free thiol groups each, were used for TNB loading in mildly basic solution (FIG. 2). The absorbance peak at 328 nm in FIG. 2, which is due to TNB and thiol mixed disulfides, shows that N1 molecules were successfully loaded with TNB. Tyrosine absorbance at 275 nm is more than 10-fold smaller than that of TNB in the near UV.

Example 2

Polypeptide Multilayer Assembly 30-layer P1/N1, P1/LN1, P1/PLGA, PLL/N1, and PLL/PLGA coatings were assembled on quartz slides by LBL. FIG. 3 presents the build up in film thickness with number of absorption steps. P1/N1 showed the largest amount of material deposited. The difference in optical mass between P1/N1 and PLL/PLGA suggests the importance of linear charge density, amino acid sequence, and degree of polymerization in multilayer film buildup, consistent with earlier work. Strong Coulombic forces will both attract oppositely-charged species and repel like-charged ones, limiting film thickness increment. The assembly of P1/LN1 resembles that of PLL/N1 and P1/PLGA. Each "loaded" TNB molecule increased peptide hydrophobicity and added a single negative charge in these experiments. Both electrostatic interactions and hydrophobic interactions influence peptide assembly behavior and film stability. The difference in assembly behavior between P1/LN1 and P1/N1 is indirect evidence of loading of N1 with TNB, consistent with the data in FIG. 3.

Polypeptide design plays an important role in the drug loading and release process described herein. TNB molecules can be loaded onto P1 and onto hen egg white lysozyme (HEWL), and that TNB can be released from the labeled molecules in solution on addition of DTT (data not shown). But neither labeled P1 nor labeled HEWL proved useful for multilayer film assembly by LBL (data not shown). P1 and HEWL are positively charged at pH 7.4, while TNB groups are negatively charged. The combination of different signs of charge in a single molecule will decrease average linear charge density and suitability for electrostatic LBL. Charge distribution in HEWL is complex, and some of the numerous hydrophobic groups present form a "hydrophobic core" in the intact native enzyme. LN1, by contrast, is useful for fabricating multilayer films by electrostatic LBL.

Example 3

Controlled TNB Release

Figure 5:
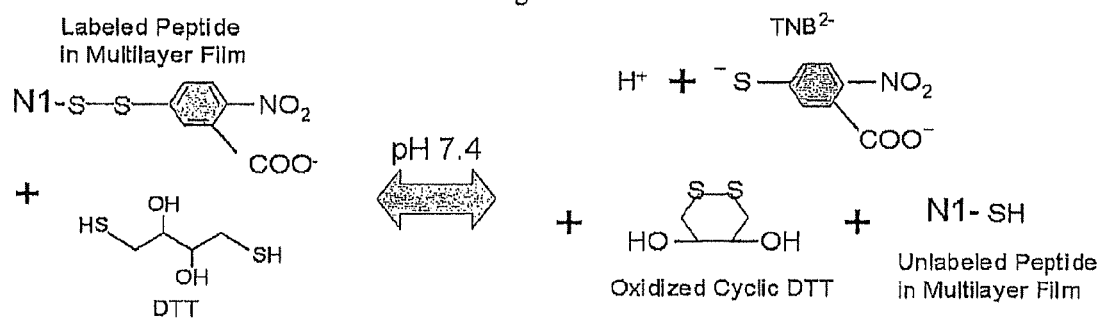
FIG. 5 shows TNB dissociation from peptide LN1 on the inward diffusion of DTT.
Figure 7:
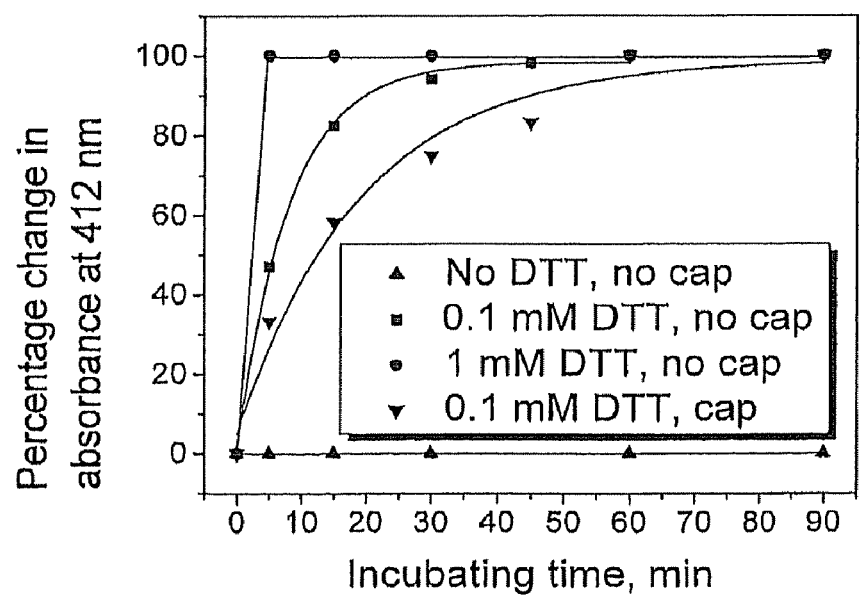
FIG. 7 shows the absorbance at 412 nm of release media for 10 P1/LN1 films v. incubation time. "Capped" films had $(P1/N1)_2$ on the outer surface. TNB release kinetics depends on redox potential and the physical behavior presented by the capping layers.
Figure 8:
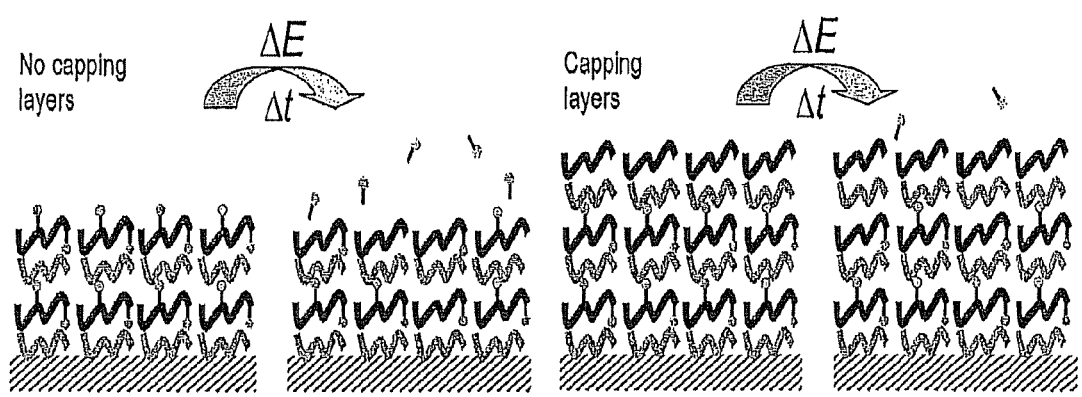
FIG. 8 shows a schematic diagram of redox-stimulated release of TNB from polypeptide multilayer nanocoatings. DTT molecules are omitted for simplicity. $\Delta E$ signifies the change in reducing potential, $\Delta t$ time.

Similar to its behavior in solution (FIG. 3), TNB was released from LN1 in multilayer coatings on immersion in an aqueous reducing environment (FIG. 5). The absorbance peak at 412 nm (FIG. 6) shows the change TNB concentration as a function of coating incubation time in 0.1 mM DTT solution. FIG. 7 compares the kinetics of TNB release from coatings with and without $(P1/N1)_2$ "capping" layers. The first-order time constant for 0.1 mM. DTT was 8 min. The higher the DTT concentration, the higher the probability of a collision of DTT with TNB in the coating in a given amount of time, and the faster the release of TNB from the coating. TNB was not released to a detectable level under mild oxidizing conditions (0 mM DTT). The concentration of TNB in 0.1 mM DTT solution after 1 hour was 2.2 µM. Addition of capping bilayers to coatings containing LN1 reduced the rate of release of TNB. The time constant for capped films was 19 min, about twice as large as for non-capped films. The capping layers contained no TNB; they could block inhibit inward diffusion of DTT and outward diffusion of TNB, and the free thiol groups could bind TNB and DTT (FIG. 8).

TNB has been "loaded" onto designed, negatively-charged, Cys-containing 32-mer polypeptides, the labeled polypeptides have been used to assemble multilayer nanocoatings by LBL, and a change in redox potential has been used to stimulate release of TNB from the coatings. The approach differs substantially from the loading of a small molecule into a coating after coating fabrication. The approach outlined here would appear to be a more efficient means of trapping a small molecule than diffusion-controlled loading, and it enables environmentally-stimulated release under specific conditions.

The use of the terms "a" and "an" and "the" and similar referents (especially in the context of the following claims) are to be construed to cover both the singular and the plural, unless otherwise indicated herein or clearly contradicted by context. The terms first, second etc. as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

---

The invention claimed is:

1. A multilayer film, the film comprising two or more layers of polyelectrolytes, wherein adjacent layers comprise oppositely charged polyelectrolytes,
   wherein a first layer polyelectrolyte comprises a first layer polypeptide comprising one or more first amino acid sequence motifs,
   wherein the one or more first amino acid sequence motifs consists of 5 to 15 amino acids and has a net charge per residue of greater than 0.4,
   wherein the first layer polypeptide is at least 15 amino acids long, and has a balance of charge at pH 7 greater than or equal to approximately one-half of the total length of the first layer polypeptide;
   wherein the first layer polypeptide comprises a therapeutic agent reversibly covalently linked to the N-terminus or the C-terminus of the first layer polypeptide; and
   wherein a second layer comprises a second layer polyelectrolyte comprising a polycationic material or a polyanionic material having a molecular weight of greater than 1,000 and at least 5 charges per molecule, wherein the second layer does not comprise a polypeptide.

2. The multilayer film of claim 1, wherein the polypeptide and the therapeutic agent both comprise sulfhydryl groups and the reversible linkage is a disulfide bond.

3. The multilayer film of claim 1, wherein an alcohol, an amine or a carboxylic acid group of the therapeutic agent is covalently attached to the N-terminus, or the C-terminus of the polypeptide.

4. The multilayer film of claim 1, wherein attachment of the therapeutic agent to the peptide is done via the incorporation of a linker between the active agent and the peptide, wherein the linker comprises a functional pendant group.

5. The multilayer film of claim 4, wherein the functional pendant group comprises a carboxylate, an alcohol, a thiol, an oxime, a hydraxone, a hydrazide, or an amine group.

6. The multilayer film of claim 1, wherein the film is in the form of a microcapsule.

7. The multilayer film of claim 1, wherein the film is formed on a substrate.

8. The multilayer film of claim 7, wherein the substrate comprises a medical device.

9. A method of controllably releasing a therapeutic agent from a polypeptide multilayer film, comprising
   providing the polypeptide multilayer film of claim 1, and
   contacting the film with a stimulus suitable to stimulate release of the therapeutic agent from the reversible linkage.

10. The method of claim 9, wherein the reversible linkage is a disulfide bond and the stimulus is a reducing agent.

11. The method of claim 9, wherein the reversible linkage is an amide, a thioester, an ester, an ether, a thioether, a carbonate, an anhydride, an orthoester, a hydroxamic acid, a hydrazone, sulfonamide, sulfonic esters, or a carbamate; and the stimulus is the pH environment of the bloodstream and/or alimentary tract.

12. The method of claim 9, wherein the stimulus is enzymatic action on the polypeptide-therapeutic agent linkage.

13. The method of claim 9, wherein the film is in the form of a microcapsule.

14. The method of claim 9, wherein the film is formed on a substrate.

15. The method of claim 14, wherein the substrate comprises a medical device.

16. A method of assembling a polypeptide multilayer film, comprising
   disposing a second layer polyelectrolyte onto a substrate, wherein the second layer polyelectrolyte comprising a polycationic material or a polyanionic material having a molecular weight of greater than 1,000 and at least 5 charges per molecule, wherein the second layer does not comprise a polypeptide; and
   disposing a first layer polypeptide on the second layer polyelectrolyte, wherein the first layer polypeptide comprises one or more first amino acid sequence motifs,
   wherein the one or more first amino acid sequence motifs consists of 5 to 15 amino acids and has a net charge per residue of greater than 0.4,
   wherein the first layer polypeptide is at least 15 amino acids long, and has a balance of charge at pH 7 greater than or equal to approximately one-half of the total length of the first layer polypeptide; and
   wherein the first layer polypeptide comprises a therapeutic agent covalently reversibly linked to the the N-terminus or the C-terminus first layer polypeptide.

17. The method film of claim 16, wherein the polypeptide and the therapeutic agent both comprise sulfhydryl groups and the reversible linkage is a disulfide bond.

18. The method of claim 16, wherein the substrate comprises a medical device.

* * * * *

SEQUENCE LISTING

```
<160> NUMBER OF SEQ ID NOS: 2

<210> SEQ ID NO 1
<211> LENGTH: 32
<212> TYPE: PRT
<213> ORGANISM: Artificial Sequence
<220> FEATURE:
<223> OTHER INFORMATION: Synthetic designed polypeptide

<400> SEQUENCE: 1

Lys Val Lys Gly Lys Cys Lys Val Lys Val Lys Gly Lys Cys Lys Val
1               5                   10                  15

Lys Val Lys Gly Lys Cys Lys Val Lys Val Lys Gly Lys Cys Lys Tyr
            20                  25                  30

<210> SEQ ID NO 2
<211> LENGTH: 32
<212> TYPE: PRT
<213> ORGANISM: Artificial Sequence
<220> FEATURE:
<223> OTHER INFORMATION: Synthetic designed polypeptide

<400> SEQUENCE: 2

Glu Val Glu Gly Glu Cys Glu Val Glu Val Glu Gly Glu Cys Glu Val
1               5                   10                  15

Glu Val Glu Gly Glu Cys Glu Val Glu Val Glu Gly Glu Cys Glu Tyr
            20                  25                  30
```